United States Patent [19]

Feinstone et al.

[11] B 4,001,391

[45] Jan. 4, 1977

[54] MEANS FOR DEPOSITING AEROSOL SPRAYS IN BUTTERY FORM

[75] Inventors: Wolffe Harry Feinstone; Fred J. Bandelin, both of Memphis, Tenn.

[73] Assignee: Plough, Inc., Memphis, Tenn.

[22] Filed: Sept. 16, 1971

[21] Appl. No.: 181,208

[44] Published under the second Trial Voluntary Protest Program on March 9, 1976 as document No. B 181,208.

Related U.S. Application Data

[63] Continuation-in-part of Ser. No. 817,572, April 18, 1969, abandoned.

[52] U.S. Cl. .................................. 424/45; 424/47; 222/4; 222/394; 222/402.1; 252/15; 252/59; 252/305; 106/10; 106/11; 106/271

[51] Int. Cl.² ..................... A61K 7/00; A61K 7/42; A61K 9/12; B65D 83/14

[58] Field of Search ................ 99/189; 424/45, 47; 222/4, 394, 402.1; 252/15, 59, 305; 106/10, 11, 271

[56] References Cited

UNITED STATES PATENTS

| 2,853,423 | 9/1958 | La Via | 424/47 |
|---|---|---|---|
| 3,079,299 | 2/1963 | Heilig | 424/45 |
| 3,135,658 | 6/1964 | Hanus et al. | 424/45 |
| 3,419,658 | 12/1968 | Sanders | 424/47 X |

FOREIGN PATENTS OR APPLICATIONS

| 1,402,092 | 4/1964 | France | 424/45 |
|---|---|---|---|
| 403,790 | 2/1965 | Japan | 424/45 |
| 383,944 | 4/1963 | Japan | 424/47 |
| 993,702 | 6/1965 | United Kingdom | 424/45 |
| 933,486 | 8/1963 | United Kingdom | 424/47 |
| 1,026,831 | 4/1966 | United Kingdom | 424/45 |

OTHER PUBLICATIONS

Sagarin, Cosmetics, Science and Technology, p. 832, Interscience Publishers, Inc., N.Y., 1957.
Wells et al., Cosmetics and the Skin, pp. 519–520, Reinhold Publishing Corp., N.Y., 1964.

*Primary Examiner*—Donald B. Moyer
*Attorney, Agent, or Firm*—Bruce M. Eisen; Stephen B. Coan

[57] ABSTRACT

Disclosed herein is an aerosol package and method using this package for dispensing substances in spray form and depositing them on a desired limited surface area in the form of a buttery, liquescent solid. The aerosol packaging contains an anhydrous, oleaginous base containing specified fats or waxes and a propellant miscible therewith.

10 Claims, No Drawings

MEANS FOR DEPOSITING AEROSOL SPRAYS IN BUTTERY FORM

This application is a continuation-in-part of our co-pending application Ser. No. 817,572, filed Apr. 18, 1969 now abandoned.

This invention relates to novel methods and compositions for dispensing substances by aerosol spray means so that they deposit onto a limited surface area in the form of a buttery solid.

Many products, particularly in the cosmetic and pharmaceutical fields, are prepared in the form of a soft buttery oleaginous base since this form permits both easy application to a limited area and uniform spreading after deposition. This butter form (commonly a cocoa butter base) further provides a pleasing and soothing feel to many users. Since it remains in a semi-solid state until manually spread, it avoids the staining and waste associated with liquid preparation.

It would be highly desirable to be able to spray a composition which can deposit on a surface, such as living skin tissue, in such buttery liquescent form. An aerosol spray, as compared to an aerosol foam or a non-aerosolized product form, possesses the advantages of being rapidly, cleanly and simply dispensable at a point conveniently remote from the desired surface target.

If one charges an aerosol container with a mixture of propellant and an oleaginous substance such as cocoa butter in the hope of producing a sprayable unguent, he will be disappointed since such a mixture produces a spray which exhibits all of the disadvantages of a liquid lotion, in that it spatters and runs and does not give the desired unguent characteristics.

We have surprisingly discovered that the foregoing object can be realized by an aerosol package comprising a pressure-resistant container, actuatable aerosol spray valve means for hermetically sealing said container and regulating the passage of material therethrough such that it leaves the terminal orifice as a finely divided spray; said container housing an anhydrous, oleaginous base containing said substance, a fat or wax in an amount of about 5 to 50% by weight of the base, said fat or wax being selected from the group consisting of stearic acid, stearyl alcohol, cetyl alcohol, and those glyceryl monoesters of fatty acids having 12 to 18 carbon atoms and those paraffin waxes having a melting point in the range of 120° to 150°F., and an effective amount of a propellant miscible with said base. Other ingredients can of course be advantageously incorporated to lend their characteristic properties to the inventive composition to enhance or extend its cosmetic, pharmaceutical or other utility.

The method aspect of this invention can be considered to reside in the method for spraying a substance such that it deposits on a desired limited surface area in the form of a buttery, liquescent solid, which method comprises orienting an aerosol package as described above such that its terminal orifice is directed toward the desired limited surface area and at a spaced distance therefrom, and actuating the aerosol spray valve means. By a "spaced distance" is meant that the product outlet should be held at least about two inches from the desired situs.

Paraffin waxes can be considered chemically as mixtures of mainly straight-chain hydrocarbons averaging 26 to 30 carbon atoms per molecule. Since they are of natural origin, they are of course commercially sold and used as cogeneric mixtures. They are generally designated by melting point ranges and tradenames. For example, Quaker State Oil Refining Corporation sells several suitable paraffin wax products under the tradename Quaker Wax having melting point ranges of 128°–132°F., 130°–132°F. and 133°–135°F., respectively. Paraffin waxes can be further refined to yield a more homogeneous product, i.e. one having a narrower melting point range. Exemplary of the latter are Esso Wax 3550 (m.p. 137°F.) and Esso Wax 4630 (m.p. 147°F.) (both available from Exxon Corporation, formerly Standard Oil Company of New Jersey). Each of the foregoing specific products can be successfully utilized as the paraffin wax component of the compositions of this invention.

The glyceryl monoester component, i.e. those monoglycerides having a melting point in the range of 120° to 150°F. and wherein the acyl moiety has between 12 and 18 carbon atoms, can either be narrow fractions such as glyceryl monostearate or broad mixtures such as Myverol Type 18-40 Distilled Monoglycerides (Distillation Product Industries).

When cetyl alcohol, stearyl alcohol, stearic acid and the glyceryl monoesters are utilized as the fat or wax component in the spray compositions of this invention, they are preferably employed in an amount of 10 to 25% by weight of the base.

The oleaginous base consists essentially of one or more animal, vegetable or mineral oils. Suitable animal oils are lanolin, neatsfoot oil, whale oil, bone oil, sperm oil, codliver oil and the like. Suitable vegetable oils are sesame oil, soya bean oil, cottonseed oil, corn oil, olive oil, peanut oil and the like. Suitable mineral oils include both light and heavy petrolatum, although the former is preferred. The oils should of course be compatible with the desired end use. For example, in aerosol packages designed for cosmetic and pharmaceutical use the oils should be cosmetically and pharmaceutically acceptable, respectively. A preferred oleaginous base for cosmetic applications comprises mineral oil and a vegetable oil. In a highly preferred embodiment a mixture of cocoa butter (theobroma oil), coconut oil, and mineral oil is used as the oleaginous base.

Those propellants widely used for cosmetic aerosols can be employed as the propellant component of the products of this invention. They are volatile materials that are gaseous at room temperature and exist largely as a liquid at those elevated pressure levels which can be practically maintained in lightweight canisters suitable for consumer use. The propellants utilized in our aerosol package must be essentially inert and be miscible with the base. They are generally employed in an amount sufficient to expel the contents of the container.

The most common chemical types used for such propellant purposes are the chlorfluoro hydrocarbons widely available under a Freon number tradename. A particularly suitable propellant for use in this invention is formed by a mixture of equal amounts of dichlorodifluoromethane (commonly sold as Freon 12) and monofluorotrichloromethane (commonly sold as Freon 11). Certain saturated hydrocarbons can also be employed as the propellant, particularly propane, butane, isobutane and cyclobutane. Although they pose a greater flammability hazard, they do possess an advantage of requiring less material by weight than the chlorfluoro hydrocarbons to perform the same propellant function. For example, isobutane can suitably be used as the propellant component in an amount as little as 10% by weight of the total spray composition whereas the chlorfluoro hydrocarbons should preferably be present in an amount of 40 to 50% by weight of the spray composition.

It can be appreciated that the aerosol packages of this invention can broadly be used for topical (cutaneous) administration of cosmetics and medicaments. They also can be advantageously used to dispense household polishing, waxing, dry cleaning, and paint removing compositions and the like. They are particularly suited to dispense emollient compositions and in a preferred embodiment they serve as suntan products by including a sunscreen agent, e.g. homomenthyl salicylate and amyl-para-dimethylaminobenzoate. They can serve as vehicles for various medicinal substances, such as hormones, antihistamines, anti-infective, anesthetics, counterirritants, keratolytics and astringents by incorporating the substance in the oil base. Although such components are preferably miscible with the base, they may also be utilizable when emulsified therewith, or in the case of a solid additive, suspended therein. The particle size should of course be sufficiently small so that they will pass through the orifice of a aerosol spray valve.

Other adjuvants can of course be incorporated into the oleaginous base appropriate to the desired end use. In accordance with standard cosmetic and pharmaceutical practice, a suitable preservative-antioxidant system is generally employed such as butylated hydroxyanisole, propyl gallate, methylparaben, propylparaben and the like. Suitable commercial mixtures of such systems can also be utilized, e.g. Tenox 2 (Eastman Chemicals). Compatible dyes and perfumes can of course be included in the compositions of this invention to enhance their consumer appeal.

The following examples illustrate representative aerosol packages of this invention. In each of the examples the aerosol package is prepared by mixing the ingredients and filling a conventional pressure-resistant aerosol canister in accordance with standard aerosol filling techniques, e.g. cold filling or pressure filling. The filled canister is sealed with a conventional aerosol spray valve having an actuator. Most importantly, the aerosol valves of the aerosol package of this invention are of the spray type as distinguished from aerosol foam valves - both being recognized as distinct entities in the aerosol are (cf. Klausner U.S. Pat. No. 3,131,153 and Sanders U.S. Pat. No. 3,419,658). The aerosol spray valve has a terminal orifice diameter generally in the range of about 0.1 to 0.03 inches, while aerosol foam valves are larger and in addition have foaming elements. Upon actuation, e.g. depressing a button on the housing, a fine spray of the base component emerges from the terminal orifice (e.g. 0.016 inch diameter) in a typical aerosol spray pattern and deposits on the skin or any other surface in the form of a soft, buttery emollient solid. This semi-solid may then be spread over the skin or other surface by the fingers or a convenient spreading aid, e.g. a cloth, in order to produce the desired emollient and covering action. The temperature of the body and/or the act of spreading liquefies the buttery solid.

Example 1 (Suntan Preparation)

| Base | Parts by Weight |
| --- | --- |
| Cocoa Butter | 250.00 |
| Coconut Oil | 25.00 |
| Paraffin, m.p. 121–132°F. (Esso) | 50.00 |
| Mineral Oil, Light (85–95SUS) | 132.75 |
| Homomenthyl Salicylate | 40.00 |
| Perfume (Oil of Rose) | 1.00 |
| Propylparaben | 1.00 |
| Butylated anisole | 0.15 |
| Propyl gallate | 0.10 |
| Contents of Aerosol Container | |
| Base | 50.00 |
| Dichlorodifluoromethane (Freon 12) | 25.00 |
| Monofluorotrichloromethane (Freon 11) | 25.00 |

Example 2 (Topical Unguent)

| Contents of Aerosol Container | Parts by Weight |
| --- | --- |
| Hydrogenated vegetable oil (Pinnacle 18, Humko) | 10.00 |
| Lanolin | 5.00 |
| Sesame Oil | 6.00 |
| Paraffin, m.p. 128–132°F. | 8.00 |
| Mineral Oil, heavy | 10.62 |
| Perfume (oil of lavender) | 0.08 |
| Propylparaben U.S.P. | 0.08 |
| Butylated hydroxy anisole | 0.02 |
| Dichlorodifluoromethane (Freon 12) | 30.00 |
| Monofluorotrichloromethane (Freon 11) | 30.00 |

Example 3 (Medicinal Preparation)

| Contents of Aerosol Container | Parts by Weight |
| --- | --- |
| Cocoa Butter | 45.00 |
| Coconut Oil | 4.00 |
| Paraffin, m.p. 121–132°F. | 14.00 |
| Mineral Oil, light | 25.40 |
| Hydrocortisone | 1.50 |
| Propyl gallate | 0.03 |
| Propylparaben | 0.07 |
| Isobutane | 10.00 |

Example 4 (Antiseptic Preparation)

| Contents of Aerosol Container | Parts by Weight |
| --- | --- |
| Cocoa Butter | 41.00 |
| Coconut Oil | 4.00 |
| Stearic Acid | 20.00 |
| Mineral Oil, light | 23.40 |
| Hexachlorophene | 1.00 |
| Methylparaben | 0.20 |
| Propylparaben | 0.20 |
| Perfume (oil of yang) | 0.20 |
| Dichlorodifluoromethane (Freon 12) | 30.00 |
| Monofluorotrichloromethane (Freon 11) | 30.00ylang) |

Example 5 (Suntan Preparation)

| Contents of Aerosol Container | Parts by Weight |
| --- | --- |
| Cocoa Butter | 10.00 |
| Coconut Oil | 4.00 |
| Stearyl Alcohol | 5.00 |
| Mineral Oil | 3.20 |
| Homomenthyl Salicylate | 17.62 |
| Butylated hydroxyanisole | 0.02 |
| Propylparaben | 0.08 |
| Perfume Oil | 0.08 |
| Dichlorodifluoromethane (Freon 12) | 30.00 |
| Monofluorotrichloromethane (Freon 11) | 30.00 |

Example 6 (Emollient Preparation)

| Contents of Aerosol Container | Parts by Weight |
| --- | --- |
| Cocoa Butter | 31.80 |

-continued
Example 6 (Emollient Preparation)

| Contents of Aerosol Container | Parts by Weight |
|---|---|
| Grape seed oil | 5.00 |
| Stearic Acid | 7.50 |
| Glyceryl Monostearate | 5.00 |
| Propyl paraben | .30 |
| Methyl paraben | .10 |
| Perfume Oil | .30 |
| Dichlorodifluoromethane (Freon 12) | 20.00 |
| Monofluorotrichloromethane (Freon 11) | 20.00 |

The substitution of the same amount of other fats or waxes outside the scope of this invention for the fats or waxes in the above examples, e.g. Carbowax 1540 (Union Carbide, m.p. 104°–122°F.), Japan Wax (Rubeco Chemicals, m.p. 128°–131°), spermaceti (m.p. 108°–121°F.), Esso Wax 1650 (m.p. 165°F.) and Esso Wax 5250 (m.p. 157°F.), results in spray compositions which deposit as oils rather than as liquescent solids.

Numerous other variants of the above compositions and methods within the scope of this invention will be apparent to those skilled in the art.

We claim:

1. An aerosol package for spraying a cosmetic or pharmaceutical substance such that it deposits on a desired limited surface area of living skin tissue in the form of a buttery, liquescent solid comprising a pressure-resistant container; actuatable aerosol spray valve means for hermetically sealing said container and regulating the passage of material therethrough such that it leaves the terminal orifice as a finely divided spray, said container housing an anhydrous cosmetically or pharmaceutically acceptable, oleaginous base containing said substance; a wax in an amount of about 5 to 50% by weight of the base, said wax being a paraffin wax having a melting point in the range of 120° to 150°F.; and an effective amount of a propellant miscible with said base.

2. An aerosol package according to claim 1 wherein said substance is a sunscreen agent.

3. An aerosol package according to claim 1 wherein said wax is present in an amount of about 10 to 25% by weight of said base.

4. An aerosol package according to claim 1 wherein said propellant comprises trichloromonofluoromethane and dichlorodifluoromethane in an amount of about 40 to 60% by weight of the total weight of the package contents.

5. An aerosol package according to claim 1 wherein said base comprises a vegetable oil and mineral oil.

6. An aerosol package according to claim 5 wherein said vegetable oil comprises coconut oil.

7. An aerosol package according to claim 5 wherein said vegetable oil comprises cocoa butter.

8. An aerosol package according to claim 7 wherein said substance is a sunscreen agent.

9. An aerosol package according to claim 8 wherein said sunscreen agent is homomenthyl salicylate.

10. A method of forming from a cosmetic or pharmaceutical substance and a base a buttery liquescent solid comprising the steps of:
   a. loading a pressure resistant container having an actuatable aerosol spray valve means for hermetically sealing said container and regulating the passage of material therethrough such that it leaves the terminal orifice as a finely divided spray; with the following:
      an anhydrous cosmetically or pharmaceutically acceptable, oleaginous base containing said substance;
      a wax in the amount of 5 to 50% by weight of said base, said wax being a paraffin wax having a melting point in the range of 120° to 150°F., and
      an effective amount of a propellant miscible with said base,
   b. directing said terminal orifice toward a desired limited surface area of living skin tissue and at a spaced distance therefrom, and
   c. spraying said base and substance by actuating said aerosol spray valve means to form said buttery liquescent solid.

* * * * *